United States Patent [19]
Ezzo et al.

[11] Patent Number: 5,142,905
[45] Date of Patent: Sep. 1, 1992

[54] OVERLAPPED TEST SPECIMEN FIXTURE

[75] Inventors: Maureen B. Ezzo, Northford; David J. Tuttle, Seymour, both of Conn.

[73] Assignee: United Technologies Corporation, Hartford, Conn.

[21] Appl. No.: 652,837

[22] Filed: Feb. 8, 1991

[51] Int. Cl.[5] .................. G01N 19/04; B32B 31/04
[52] U.S. Cl. ............................. 73/150 A; 156/378
[58] Field of Search ............. 73/150 A; 374/45; 264/40.1; 156/359, 378

[56] References Cited

U.S. PATENT DOCUMENTS

| | | | |
|---|---|---|---|
| 4,768,376 | 9/1988 | Lanham, Jr. et al. | 73/150 A |
| 4,770,835 | 9/1988 | Kromrey | 264/257 |
| 4,787,952 | 11/1988 | Broz et al. | 73/150 A |
| 4,856,162 | 8/1989 | Graff et al. | 264/40.1 X |
| 4,940,563 | 7/1990 | Kromrey | 264/313 X |

*Primary Examiner*—Daniel M. Yasich
*Attorney, Agent, or Firm*—Terrance J. Radke

[57] ABSTRACT

An overlapped test specimen fixture operates as a template to precisely position pairs of standardized coupons in predetermined overlapped relation to demarcate standardized bonding sites for application of adhesive systems to be tested. The fixture includes a caul plate bounded by an integral, elevated shoulder having opposed sidewalls and endwalls. The exposed surface is configured as a bi-level, flat support surface having upper and lower surfaces that support the coupons in overlapping relation. The opposed sidewalls are operative to precisely position overlapped coupons lengthwise wherein such coupons demarcate a predetermined overlap length. The fixture also includes locator rails extending upwardly from support surfaces which are operative to precisely position the overlapped coupons transversely. The precisely positioned, overlapped coupons define standardized bonding sites for application of the adhesive system to form a test specimen. Securing members are utilized to temporarily secure test specimens in immobile combination with the support surfaces. The fixture may be used to cure test specimens in room temperature, oven, or autoclave environments. For autoclave use, the upper edges of the elevated shoulder are configured for sealing with vacuum bagging material that envelops the test specimens secured to the support surfaces. The fixture further includes a continuous vent channel formed in the support surfaces to facilitate, evacuation of the fixture and a port formed in one endwall that is configured to fluidically connect the vacuum source to the continuous vent channel wherein a vacuum may be drawn about test specimens enveloped by vacuum bagging material.

14 Claims, 4 Drawing Sheets

OVERLAPPED TEST SPECIMEN FIXTURE

TECHNICAL FIELD

The present invention relates to test apparatus, and more particularly, to an overlapped test specimen fixture that provides reproducible, standardized test specimens for characterization testing of adhesive systems.

BACKGROUND ART

Many manufacturing and/or assembly processes (generically production processes) require that structural elements of similar or dissimilar materials be secured in combination. One method employed in such production processes to secure structural elements in combination is to provide an adhesive bond between the structural elements. One critical feature of such production processes is the nature, i.e., characteristics or properties, of the adhesive system (film or paste adhesives) that provides the bonding force. Characterization testing for adhesive systems generally involves applying an adhesive system between overlapping structural elements, and curing the adhered, overlapped structural elements to form a bonded test specimen which may then be subjected to various mechanical and/or chemical tests.

Industry performs characterization testing of adhesive systems to verify, establish and/or define the properties of adhesive systems, e.g., shear strength, cure temperature, cure pressure, which make various adhesive systems effective bonding agents in different production processes. Characterization databases for adhesive systems are continually being updated and/or expanded to provide industry with current knowledge regarding the properties of various adhesive systems. In the aerospace industry alone, over one hundred different adhesive systems are available as bonding agents for production processes. Moreover, approximately twelve new adhesive systems are developed each year for bonding applications in aerospace production processes.

In performing characterization testing o adhesive systems to develop property databases for adhesive systems, it is extremely important that the testing procedure produce both standardized and reproducible test results for comparative purposes, i.e., the properties of the adhesive systems are not subjected to test specimen and/or fixture induced variabilities. Standardization ensures that evaluation and selection of an adhesive system for a specific production process application is based upon a logical and reliable foundation.

A number of factors are involved in ensuring that standardized and reproducible test results are achieved in characterization testing of adhesive systems. The first and foremost factor to be considered is the test specimen bonding site, i.e., the bonding area to which the adhesive system to be tested is applied, which must be constant for all characterization testing. The size of the bonding site directly influences the strength of the resultant adhesive system bond, and inadvertent variations in the size of the test specimen bonding sites result in unreliable characterization databases. The other primary factor for consideration is that the fixture utilized to prepare test specimens must facilitate curing of the adhesive system being tested under conditions that approximate as closely as possible the curing conditions that will be encountered in actual production processes.

A number of adhesive systems are characterized by room temperature or oven curing (elevated temperatures) cycles at a constant cure pressure. Such adhesive systems may be readily evaluated to provide data for adhesive systems property databases using a simple, spring-loaded jig fixture JF of the type illustrated in FIG. 1. One or more test specimens, formed by overlapping pairs of coupons and interposing the adhesive system to be characterized in the bonding site defined by the overlap area of the coupons, are disposed in the jig fixture JF. The jig fixture JF is operative to apply a constant mechanical pressure over the bonding site. Such a jig fixture JF is generally satisfactory for room temperature or oven cured adhesive systems. However, since the test specimens are not totally secured by the jig fixture JF, bonding site variations may be induced in test specimens through careless handling of the jig fixture JF during the preparation process. Also, the jig fixture JF is per se limited to applying a single constant pressure to the bonding site during cure of the adhesive system.

With the advent of new production processes and/or new structural materials, for example, production processes involving composite materials, a need has emerged to provide standardized and reproducible characterization of adhesive systems used in such new production processes, and especially those that involve bonding of composite structural materials As discussed above, such characterization schemes should emulate as closely as possible the conditions inherent in the actual production processes so that adhesive systems may be characterized in terms of actual production applications.

For example, autoclave or Therm-X TM (see, e.g., U.S. Pat. Nos. 4,940,563 and 4,770,835) production processes are being more frequently utilized by industry, especially the aerospace industry, to fabricate composite structures. Such production processes require adhesive bonding of structural materials that are encapsulated in specialized sealed vacuum bagging films, which are then evacuated so that the vacuum bagging material contacts the structural material. The encapsulated materials are then inserted in a fluid-pressurized autoclave, and subjected to cure cycles that generally comprise variable fluid pressures and temperatures over time.

The prior art jig fixture JF described hereinabove, however, is only capable of applying a constant force over time, and, as such, is not suitable for use in autoclave-type curing processes. Moreover, the bulky structure of the prior art jig fixture JF is not readily amenable to encapsulation within vacuum bagging material. Furthermore, the complex configuration of the prior art jig fixture JF may cause damage to the vacuum bag material during handling and/or cure processing.

Industry has endeavored to develop a fixture for producing test specimens that is compatible with the autoclave-type cure environment to produce standardized test specimens for adhesive systems characterization testing. Test specimens, which comprise overlapped standardized coupons with the adhesive system to be tested applied thereto, have been assembled on a flat base plate fixture, encapsulated in vacuum bag material, evacuated, and cured in an autoclave-type environment Test specimens produced in this manner, however, were found to have been subjected to skewing and/or wedging effects during handling and/or the curing process that resulted in marked variations in bonding site areas, i.e., the test specimens were not usable for adhesive systems characterization testing.

To prevent skewing and/or wedging effects, test specimens were taped to the base plate fixture Such test specimens were still found to have cure process and/or handling induced variations in bonding site areas. Pencil marks were used to define test specimen bonding site areas in the hopes of producing test specimens having constant area bonding sites It was discovered, however, that the pencil lead was inducing premature fractures in the adhesive bonds. Attempts were made to define the bonding sites using masking tape. The masking tape, however, was found to introduce entrapped air in the adhesive bonds.

A need exists for an adhesive systems test specimen fixture that can be used in an autoclave-type environment and which will produce test specimens having constant area bonding sites, which may then be used for characterization testing of adhesive systems. Such a fixture should be operative to precisely position pairs of standardized coupons in overlapped relation to demarcate standardized bonding sites, i.e., constant area bonding sites. Such a fixture should also include means to secure precisely positioned test specimens to prevent skewing and/or wedging of test specimens during handling and/or cure processing. The fixture may have a configuration which facilitates envelopment of the test specimens within vacuum bagging material rather than encapsulating the entire fixture.

Preferably the fixture may also include an integral means for interconnecting the fixture, rather than the vacuum bagging material, directly to a vacuum source. Generally, prior art autoclave fixturing assemblies utilized a portable vacuum source port connector that was connected directly to the vacuum bagging material. Such a connection tended to induce tears in the vacuum bagging material.

DISCLOSURE OF THE INVENTION

An overlapped test specimen (OTS) fixture according to the present invention overcomes the inherent limitations of prior art adhesive system test specimen fixtures by consistently producing test specimens having standardized bonding sites, i.e., constant area bonding sites. The OTS fixture of the present invention is configured for use in an autoclave-type environment, and may also be used for room temperature and oven temperature cure cycles. The OTS fixture of the present invention is operative as a template to precisely position pairs of standardized adherents or coupons in a predetermined overlapped relation to define respective test specimens having standardized bonding sites, i.e, constant bonding areas defined by the dimensions of the standardized coupons and the predetermined overlap length of each pair of precisely positioned coupons. The standardized bonding sites accommodate adhesive systems to be tested. Test specimens prepared with the OTS fixture allow valid evaluations and comparisons to be made among test data derived from characterization testing of such test specimens.

The OTS fixture of the present invention also includes means to temporarily secure each precisely positioned test specimen in immobile combination to the OTS fixture. The securing means ensures that no variability is induced in the standardized bonding sites during cure processing and/or fixture handling. Furthermore, the securing means detachably secures each precisely positioned test specimen in combination with the OTS fixture in such manner that variable pressure forces may be exerted against respective standardized bonding sites during an autoclave-type curing process as well as constant pressure forces during room temperature and oven curing cycles. The configuration of the OTS fixture of the present invention facilitates sealing of vacuum bagging material in combination with the OTS fixture to envelop the test specimens rather than encapsulating the entire fixture. The configuration of the OTS fixture further includes integral continuous vent channel means to facilitate drawing an internal vacuum in the enveloped OTS fixture.

In addition, the OTS fixture also includes integral means for interconnecting an enveloped OTS fixture with a vacuum source so that a vacuum may be drawn in the enveloped OTS fixture The configuration of the OTS fixture, as enveloped and integrated with a vacuum source, facilitates loading (or unloading) from an autoclave for curing of the test specimens.

The OTS fixture is preferably formed as an integral structure from a structurally rigid, temperature resistant material such as steel. Inasmuch as the structural configuration of the OTS fixture is operative as a precise positioning template, the OTS fixture must be fabricated to precise dimensions within strict tolerances. Any conventional fabrication technique may be utilized to form OTS fixtures according to the present invention, as long as the technique utilized ensures the precise dimensioning required. A fabricated OTS fixture may be plated with a material such as nickel to prevent nicking and/or scratching of the OTS fixture during positioning and removal of test specimens.

The OTS fixture of the present invention comprises a caul plate and an integral, raised shoulder that forms a peripheral boundary about an exposed surface of the caul plate. The upper edges of the shoulder are flat to facilitate sealing of a vacuum bagging material to the OTS fixture so as to envelop only the exposed surface of the caul plate.

The raised, peripheral shoulder includes opposed endwalls and opposed sidewalls, the spacing between internal faces of the opposed sidewalls facilitating precise lengthwise positioning of pairs of standardized coupons with respect to one another. The exposed surface of the caul plate is configured as a bi-level, flat support surface comprising upper and lower support surfaces that are operative to support respective pairs of standardized coupons defining each test specimen in a predetermined overlapped relation.

A plurality of integrally formed locator rails, extending upwardly from the upper and lower support surfaces, are operative for precise transverse positioning of corresponding pairs of standardized coupons. A coupon securing means for the OTS fixture is operative to temporarily secure each pair of precisely positioned standardized coupons comprising a test specimen to the upper and lower support surfaces of the caul plate.

A continuous vent channel is formed throughout the bi-level, flat support surface to facilitate drawing an internal vacuum within an enveloped OTS fixture and to ensure that external pressure forces applied through the vacuum bagging material are uniformly transmitted to the test specimens. The continuous vent channel extends across the caul plate between the opposed endwalls, adjacent the locator rails, adjacent to portions of the opposed sidewalls, and transversely between locator rails. A major portion of the continuous vent channel underlies the test specimens precisely positioned within the OTS fixture to ensure that a vacuum is evenly drawn within the enveloped OTS fixture, and that the external fluid pressure forces of an autoclave-type environment are evenly applied to test specimens.

The OTS fixture also includes integral means, in fluidic communication with the continuous vent channel, for readily interconnecting a vacuum source directly to the OTS fixture. The vacuum interconnect means allows a vacuum line having an integral end connector, connected to an external vacuum source, to be quickly and easily integrated with the OTS fixture. The vacuum interconnect means eliminates the need to connect the vacuum source directly to the vacuum bagging material, thereby greatly improving the durability and reliability of the OTS fixture over prior art systems.

To use the OTS fixture of the present invention, pairs of standardized coupons are precisely positioned on the bi-level support surface of the OTS fixture as described hereinabove. The adhesive system to be tested is applied to the standardized bonding sites demarcated by each pair of overlapped coupons, and the coupon securing means is used to lock individual test specimens, as precisely positioned, within the OTS fixture. The OTS fixture is then utilized to cure the test specimens in an autoclave, room temperature, or oven environment.

For an autoclave environment, vacuum bagging material is sealed to the upper edges of the peripheral shoulder, a vacuum source interconnected to the OTS fixture via the vacuum interconnect means, and a vacuum drawn within the enveloped OTS fixture. The vacuumized, enveloped OTS fixture is loaded into an autoclave and subjected to an autoclave-type curing cycle, i.e., variable pressures and variable temperatures, to cure the adhesive system. After completion of the cure cycle, the OTS fixture is unloaded from the autoclave, the vacuum bagging material removed, and the cured test specimens released from the support surface and removed from the OTS fixture. The cured test specimens may be processed to produce overlap bonded test strips that may be utilized for characterization testing to define the properties of the adhesive bond.

The OTS fixture according to the present invention consistently produces process test specimens having standardized bonding sites. The OTS fixture of the present invention has significantly reduced the number of test specimen rejects, i.e., test specimens unsuitable for characterization testing.

The foregoing and other features and advantages of the present invention will become more apparent from the following description and accompanying drawings.

BEST MODE FOR CARRYING OUT THE INVENTION

Figure 2:
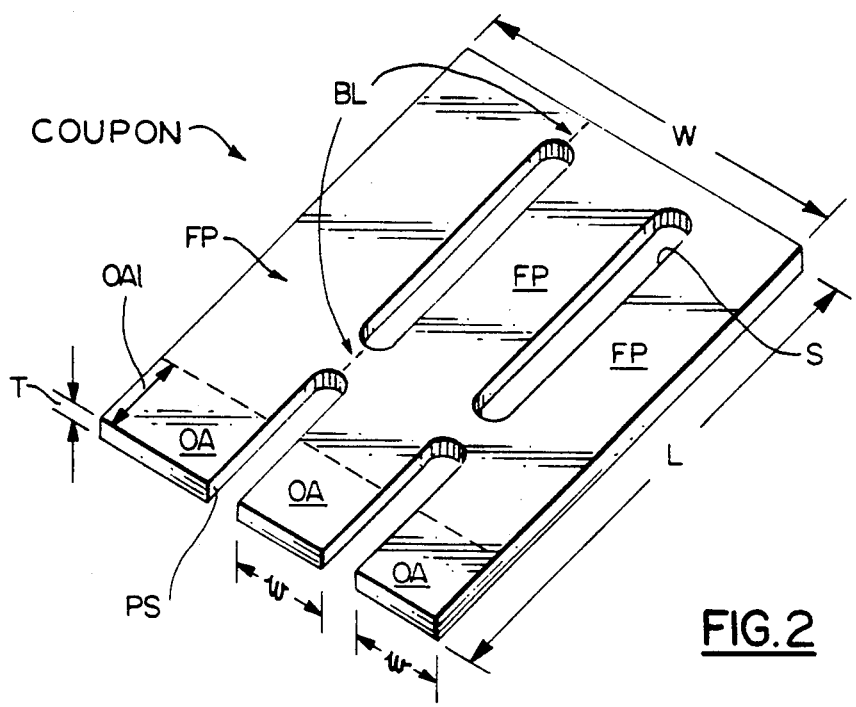
FIG. 2 is a perspective view of a standardized test coupon.

Referring now to the drawings wherein like reference letters/numerals identify corresponding or similar elements throughout the several views, FIG. 2 illustrates a standardized adherent or coupon C. Such standardized coupons C are commercially available and are generally utilized by industry, especially the aerospace industry, to form test specimens for characterization testing to generate generalized property databases for adhesive systems.

The standardized coupon C is formed from an aluminum alloy such as 2024-T3, and has an overall length L of about $5.0 \pm 0.03$ inches, an overall width W of about $3.50 \pm 0.03$ inches, and a thickness T of about $0.063 \pm 0.01$ inches. Each coupon C has slots S and partial slots PS formed therethrough so as to define three finger panels FP per coupon C. Each finger panel FP has a width w of about $1.0 \pm 0.01$ inches. An overlap area OA having a predetermined overlap length OA1 is defined at the end of each finger panel FP. Per the convention of the assignee of the present invention and the aerospace industry in general, the predetermined overlap length OA1 of the overlap area OA is about 0.5 inches. Break lines BL are defined between adjacent finger panels FP as illustrated in FIG. 2.

Prior to use, the standardized coupons C are prepared for bonding. For example, in one preparation method the coupons C are first vapor degreased, and then anodized by means of an anodizing agent such as chromic acid. The finger panels FP of each coupon C are then primed with an epoxy-based primer, priming being effected to ensure that at least the overlap area OA of each finger panel FP is primed. The primer layer has a predetermined thickness that is constant for the finger panels FP of each coupon C.

Figure 3:
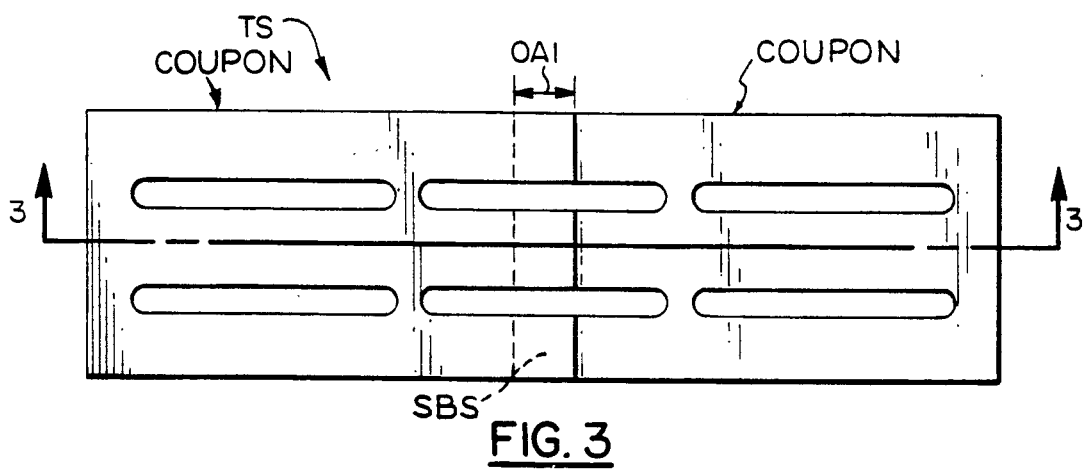
FIG. 3 is a plan view of a test specimen formed by overlapped test coupons.
Figure 4:
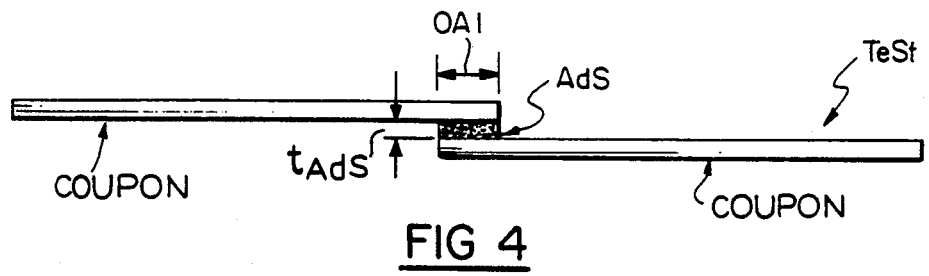
FIG. 4 is a cross-sectional view of the test specimen of FIG. 3 taken along line 3—3.

To form a test specimen TS, a pair of prepared, standardized coupons C are overlapped as illustrated in FIGS. 3, 4. An overlapped test specimen fixture according to the present invention, discussed in further detail hereinbelow, ensures that the corresponding pair of coupons C comprising each test specimen TS are correctly positioned so as to provide standardized bonding sites SBS (three) for each test specimen TS. Corresponding coupons C are overlapped in such a manner that the overlap areas OA of the finger panels FP of the respective coupons C are superposed by the predetermined overlap length OA1, the superposed overlap areas OA of respective finger panels FP demarcating the standardized bonding sites SBS. Based upon the preceding disclosure regarding the standardized coupons C, each standardized bonding site SBS has an area defined by (w X OA1), i.e., ($1.0 \pm 0.01$ inches) X (0.5 inches). The adhesive system AdS to be characterized is applied to each standardized bonding site SBS defined by the superposed overlap areas OA as illustrated in FIG. 4.

Once a given test specimen TS has been processed, i.e., the adhesive system AdS applied to the standardized bonding sites SBS of the respective finger panels FP has been cured according to a particular curing protocol, the test specimen TS may be broken down by separating such test specimen TS along the break lines BL of the respective coupons C. Separation may be effected by any conventional technique such as laser cutting, machine cutting, etc.

Each test specimen TS, therefore, provides three individual overlap bonded test strips TeSt. Each overlap bonded test strip TeSt may be utilized for characterization testing of the adhesive system AdS, as for example, by subjecting an overlap bonded test strip TeSt to tensile testing to define the shear strength of the adhesive system AdS.

An exemplary embodiment of an overlapped test specimen (OTS) fixture 10 according to the present invention is illustrated in FIGS. 5-8. The OTS fixture 10 of the present invention is operative as a template to precisely position pairs of standardized coupons C comprising respective test specimens TS to demarcate standardized bonding sites SBS, i.e, constant bonding areas defined by the relevant dimensions of the standardized coupon C, which for the standardized coupon C described in the preceding paragraphs is equal to (w $\times$ OA1).

The standardized bonding sites SBS are utilized for the application of adhesive systems AdS to be tested. Since the standardized bonding sites SBS have constant bonding areas, valid evaluations and comparisons may be made among test data derived from characterization testing of test strips TeSt derived from different test specimens TS.

The OTS fixture 10 of the present invention also includes means to temporarily secure each precisely positioned test specimen TS in immobile combination to the OTS fixture 10. The securing means ensures that no variability is induced in the standardized bonding sites SBS during cure processing and/or fixture handling. Furthermore, the securing means detachably secures each precisely positioned test specimen TS in combination with the OTS fixture 10 in such manner that variable pressure forces may be exerted against respective standardized bonding sites SBS during an autoclave-type curing process. The OTS fixture 10 may also be utilized in room temperature or oven curing cycles with constant applied pressures. The configuration of the OTS fixture 10 of the present invention facilitates sealing of vacuum bagging material (not shown) in combination with the OTS fixture 10 to envelop the test specimens TS, rather than encapsulating the entire fixture. The configuration of the OTS fixture 10 further includes integral continuous vent channel means to facilitate drawing an internal vacuum in the enveloped OTS fixture 10.

In addition, the OTS fixture 10 also includes integral means, fluidically communicating with the continuous vent channel means, for interconnecting an enveloped OTS fixture 10 with a vacuum source so that a vacuum may be drawn in the enveloped OTS fixture 10. The configuration of the OTS fixture 10, as enveloped and integrated with a vacuum source, facilitates loading (or unloading) from an autoclave (not shown) for curing of the test specimens TS.

The OTS fixture 10 is preferably formed as an integral structure from a structurally rigid, temperature resistant material such as steel, e.g., 4130 steel. By temperature resistant is meant that the material of the OTS fixture 10 has a coefficient of thermal expansion such that the OTS fixture 10 experiences no (or minimal) dimensional changes when exposed to the elevated temperatures required to cure the adhesive system AdS being tested, e.g., during an autoclave cure cycle.

Inasmuch as the OTS fixture 10 acts as a precise positioning template, the OTS fixture 10 must be fabricated to precise dimensions within strict tolerances. The embodiment of the OTS fixture 10 illustrated in FIGS. 5-8 has been fabricated by milling a steel blank to form the features of the invention described hereinbelow in further detail. It will be appreciated that other conventional fabrication techniques may be utilized to form OTS fixtures according to the present invention, as long as the technique ensures the precise dimensioning required. A fabricated OTS fixture 10, as described in further detail in the following paragraphs, may be plated with a material such as nickel to prevent nicking and/or scratching of the OTS fixture 10 during positioning or removal of test specimens TS.

Figure 5:
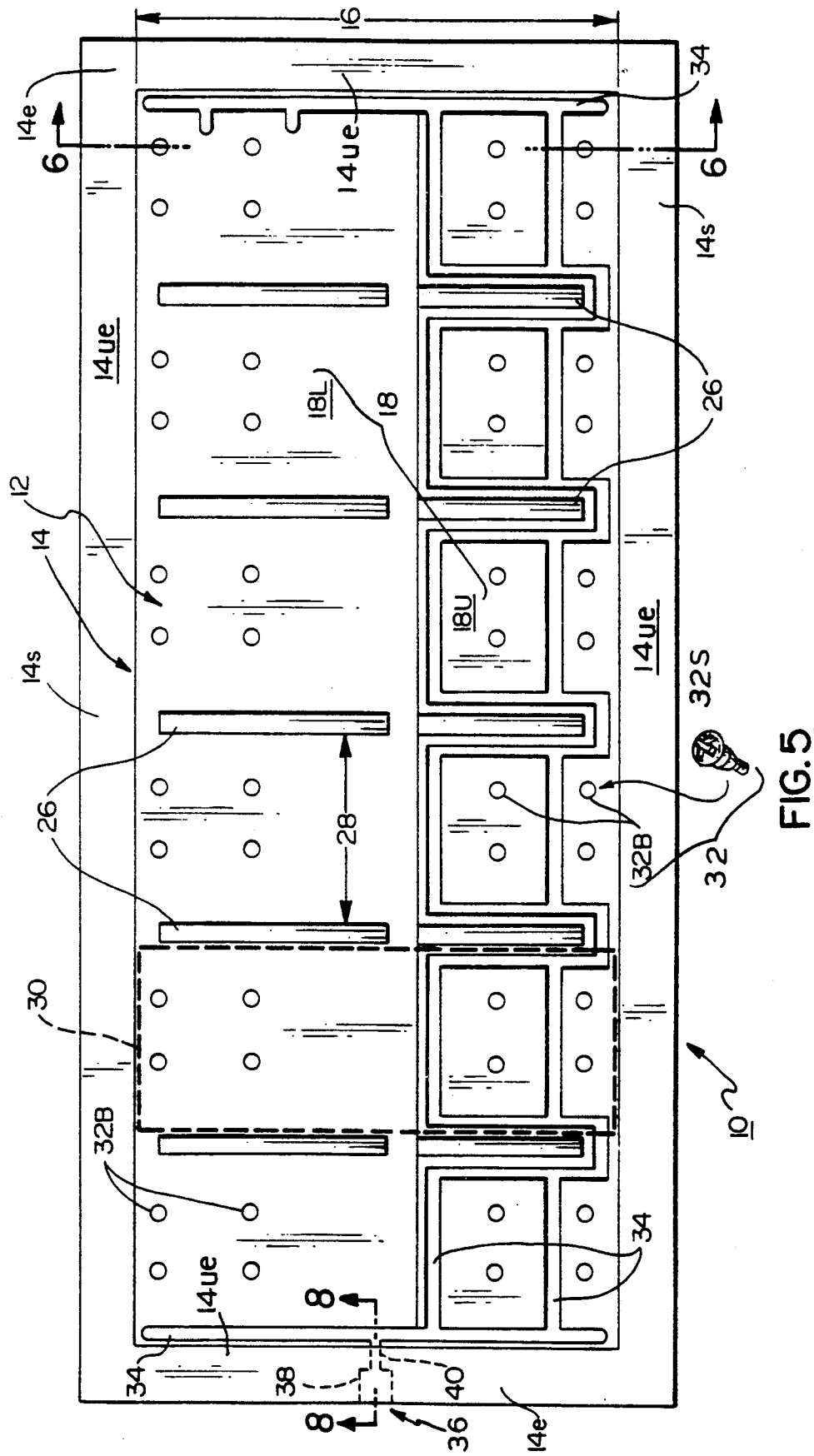
FIG. 5 is a perspective view of an overlapped test specimen fixture according to the present invention.
Figure 6A:
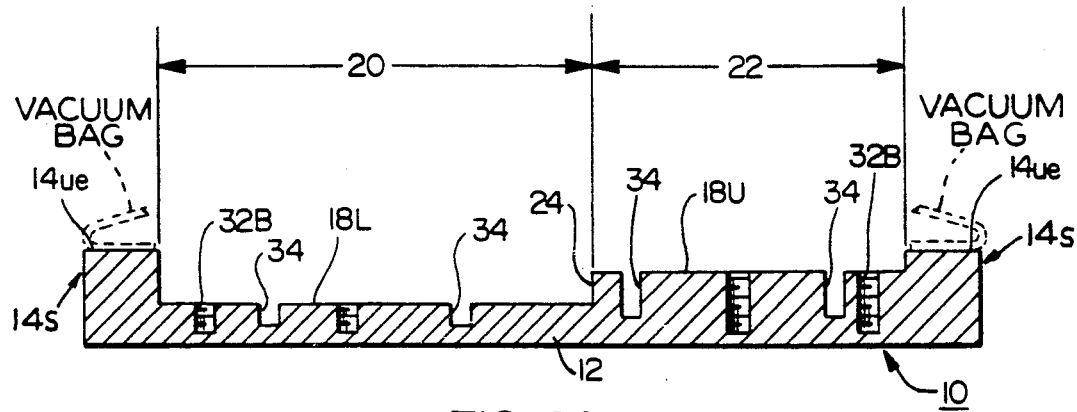
FIG. 6A is a cross-sectional view of the overlapped test specimen fixture of FIG. 5 taken along line 6—6.
Figure 6B:
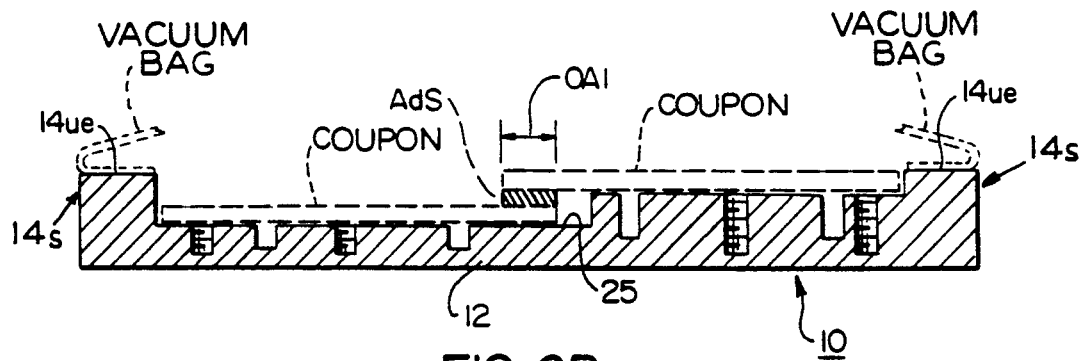
FIG. 6B is the cross-sectional view of FIG. 6A illustrating a pair of standardized coupons positioned in the fixture.

The OTS fixture 10 embodiment illustrated in FIG. 5 has overall dimensions of about 27 inches (length), about 12 inches (width), and about 0.625 inches (height). The OTS fixture 10 comprises a caul plate 12 and a raised, peripheral shoulder 14 (see also FIGS. 6A, 6B). The upper edges 14$ue$ of the raised, peripheral shoulder 14, as illustrated in FIGS. 6A, 6B are flat to facilitate sealing of a vacuum bagging material (not shown) thereto so as to envelop only the exposed surface of the caul plate 12.

The raised peripheral shoulder 14 includes opposed endwalls 14$e$ and opposed sidewalls 14$s$. The sidewall spacing 16 (between the internal faces of the opposed sidewalls 14$s$, as illustrated in FIG. 5) of the OTS fixture 10 facilitates precise lengthwise positioning of each pair of standardized coupons C with respect to one another, i.e., the ends of the coupons C abut corresponding internal faces of the opposed sidewalls 14$s$. The distance 16 between the internal faces of the opposed sidewalls 14$s$ is equal to about twice the length L of a standardized coupon C minus the defined overlap length OA1 of the overlap area OA that defines the standardized bonding site SBS, i.e., the sidewall spacing 16 is approximately equal to (2L - OA1). Based upon the dimensions of the standardized coupon C described hereinabove, the sidewall spacing 16 of the OTS fixture 10 embodiment illustrated in FIG. 5 is about 9.50.

The exposed surface of the caul plate 12 bounded by the internal faces of the raised, peripheral shoulder 14 is configured as a bi-level, flat support surface 18 that is operative to support each pair of standardized coupons C comprising on test specimen TS as illustrated generally in FIG. 5. The bi-level configuration of the support surface 18, as more clearly illustrated in FIGS. 6A, 6B, is a stepped configuration that supports corresponding pairs of standardized coupons C comprising a test specimen TS in the predetermined overlapped configuration defined by the OTS fixture 10 configuration, as illustrated in FIG. 6B. The lower level 18L of the support surface 18 has a length 20 and the upper level 18U of the support surface 18 has a length 22, the upper and lower support surfaces 18U, 18L being separated by a spacing shoulder 24 having a predetermined height.

The length 20 of the lower support surface 18L is slightly greater than the overall length L of a standardized coupon C. With reference to FIG. 6B, such a length 20 for the lower support surface 18L creates a bleed space 25 between the end of the standardized coupon C and the spacing shoulder 24. This volume 25 is operative to accommodate any excessive adhesive AdS that may bleed from the standardized bonding sites SBS. The length 22 of the upper support surface 18U, in contrast, is less than the overall length L of a standardized coupon C. A standardized coupon C positioned on the upper support surface 18U extends outwardly past the spacing shoulder 24 by the length of the bleed space 25 plus the defined overlap length OA1.

The predetermined height of the spacing shoulder 24 is based upon the thickness T of a standardized coupon C plus the thickness $t_{AdS}$ of the adhesive system AdS applied to the standardized bonding site SBS. Typically the thickness $t_{AdS}$ of the applied adhesive system AdS is about 0.005 inches.

Based upon the dimensions of the standardized coupon C described hereinabove, the lower support surface 18L of the OTS fixture 10 embodiment illustrated in FIGS. 5-8 has a length 20 of about 5.125 inches (about 0.125 inches comprising the length of the bleed space 25), the upper support surface 18U has a length 22 of about 4.375 inches, and the vertical spacing 24 is about 0.068 inches. Both the upper and lower support surfaces 18U, 18L are spaced apart (downwardly) from respective upper edges 14ue of the corresponding sidewalls 14s. For the embodiment of the OTS fixture 10 illustrated in FIGS. 6A, 6B, the upper support surfaces 18U is spaced apart by a distance of about 0.063 inches and the lower support surface 18L is spaced apart by a distance of about 0.136 inches.

Figure 1:
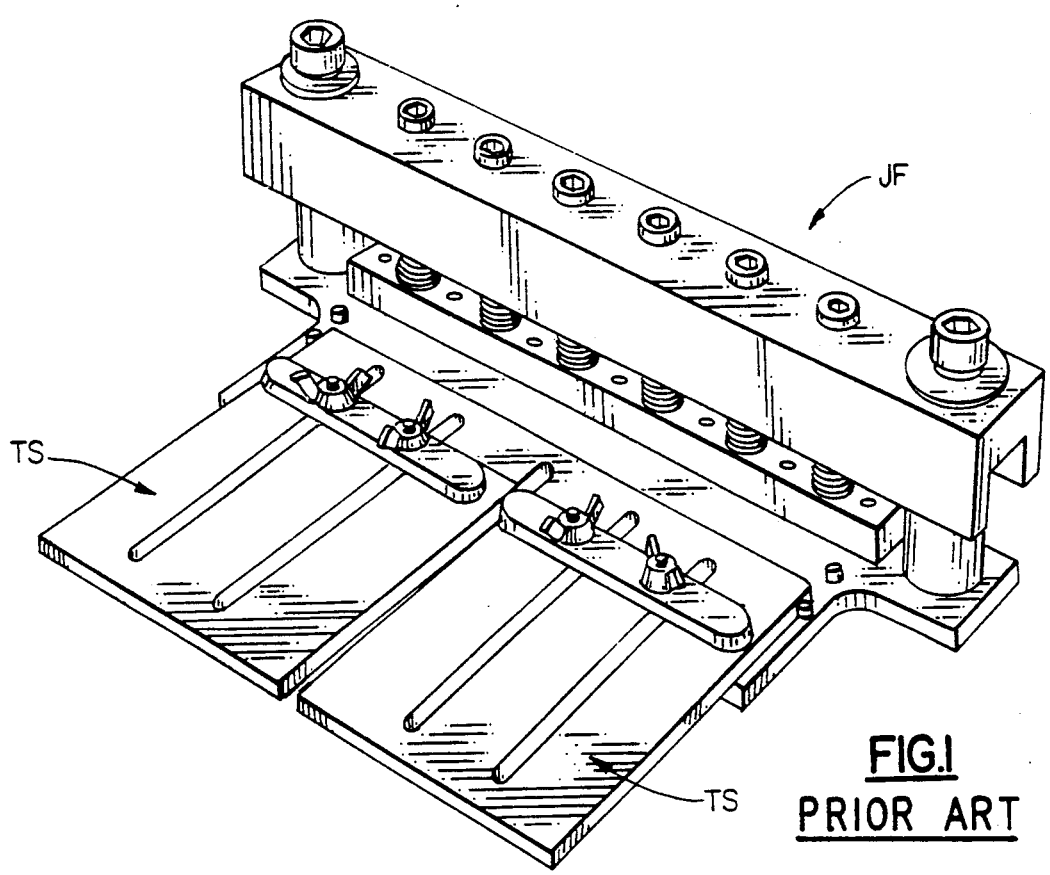
FIG. 1 is a perspective view of a prior art jig fixture.
Figure 7:
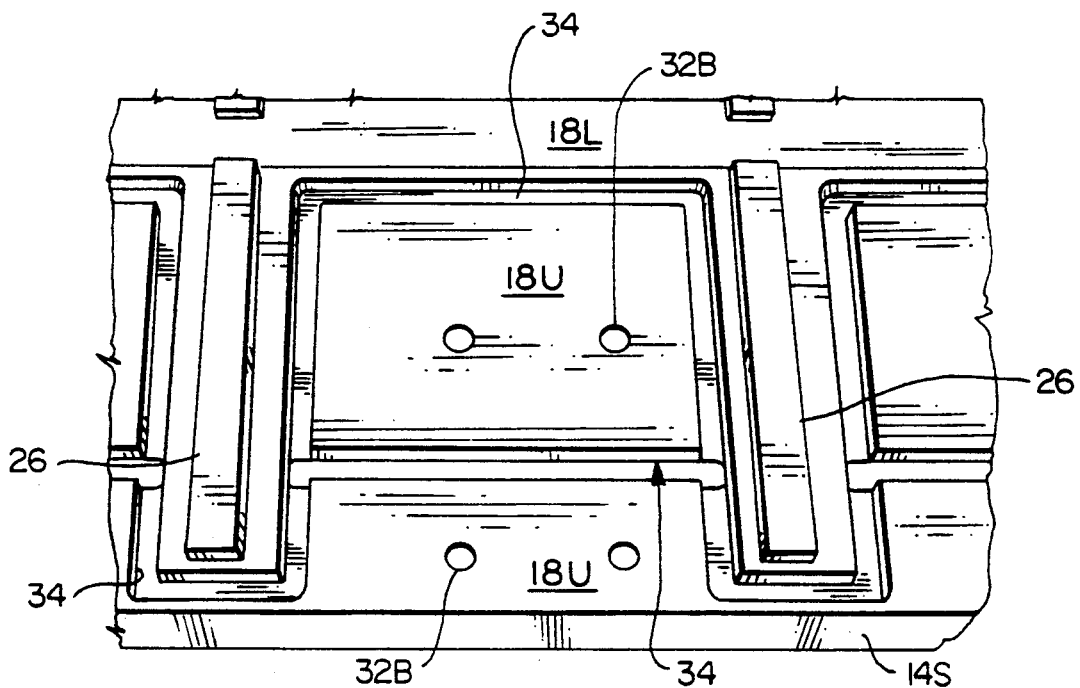
FIG. 7 is an enlarged, partial perspective view of the fixture of FIG. 5.

A plurality of integrally formed locator rails 26, as illustrated in FIGS. 5, 7 extend upwardly from the upper and lower support surfaces 18U, 18L comprising the bi-level, flat support surface 18. The locator rails 26 are operative for precise transverse positioning of each corresponding pair of standardized coupons C, i.e., one side of each coupon C abuts one adjacent locator rail 26 (for the test specimens TS disposed at the ends of the OTS fixture 10, the respective standardized coupon C may abut an internal face of the corresponding endwall 14e). The spacing 28 between adjacent locator rails 26 (or the locator rail 26 and the internal face of the corresponding endwall 14e) is slightly greater than the width W of the standardized coupon C. Based upon the dimensions of the standardized coupon C described hereinabove, the spacing 28 of the OTS fixture 10 embodiment illustrated in FIG. 5 is slightly greater than about 3.50 inches.

For convenience of description, each pair of standardized coupons C precisely positioned in the OTS fixture 10 as described in the preceding paragraphs may be defined as occupying a stall 30 of the OTS fixture 10. Each stall 30 may be identified as the area bounded by adjacent locator rails 26 (or the corresponding endwall 14e) and the corresponding portions of the opposed sidewalls 14s. An exemplary stall 30 is identified by the closed dashed line illustrated in FIG. 5. The OTS fixture 10 embodiment illustrated in FIG. 5 has six stalls 30 such that up to six test specimens TS may be prepared at a time. It will be appreciated that an OTS fixture may be fabricated having more or less than six stalls 30.

The coupon securing means 32 for the OTS fixture 10 embodiment illustrated in FIGS. 5, 6 comprises a plurality of threaded bores 32B and a corresponding plurality of round-headed securing screws 32S. The coupon securing means 32 is operative to temporarily secure each pair of standardized coupons C precisely positioned in a stall 30 in immobile combination with the upper and lower support surfaces 18U, 18L. Round-headed securing screws 32S are used to minimize damage to the vacuum bagging material that may be utilized to envelope the bi-level, flat support surface 18 of the OTS fixture 10. The threaded bores 32B are formed in the upper and lower support surface 18U, 18L of each stall 30 in alignment with corresponding slots S and partial slots PS of the pair of standardized coupons C precisely positioned therein as illustrated in FIGS. 5, 7.

Once each pair of standardized coupons C is precisely positioned within a stall 30, securing screws 32S are inserted through respective slots S and partial slots PS of the standardized coupons C and threaded into corresponding threaded bores 32B to immobilize the coupons C. The coupon securing means 32 may be disengaged after the test specimens TS have been cured to release (and remove) the test specimens TS from the OTS fixture 10.

A continuous vent channel 34 is formed throughout the bi-level, flat support surface 18 of the OTS fixture 10 as illustrated in FIG. 5 (see also FIGS. 6A, 6B, 7). The continuous vent channel 34 facilitates drawing an internal vacuum within an enveloped OTS fixture 10, and moreover, ensures that external pressure forces applied through the vacuum bagging material, e.g., during an autoclave cure cycle, are uniformly transmitted to the test specimens TS precisely positioned on the support surface 18 of the OTS fixture 10. The continuous vent channel 34 extends between the opposed endwalls 14e, and generally adjacent the locator rails 26 and segments of the opposed sidewalls 14s, as illustrated in FIG. 5. The continuous vent channel 34 also extends transversely across the various stalls 30. A major portion of the continuous vent channel 34 underlies the test specimens TS precisely positioned within the stalls 30 of the OTS fixture 10. The aforedescribed configuration of the continuous vent channel 34 ensures that a vacuum is evenly drawn within the enveloped OTS fixture 10 and that the external fluid pressure forces of an autoclave-type environment are uniformly applied to test specimens TS precisely positioned in the OTS fixture 10.

Figure 8:
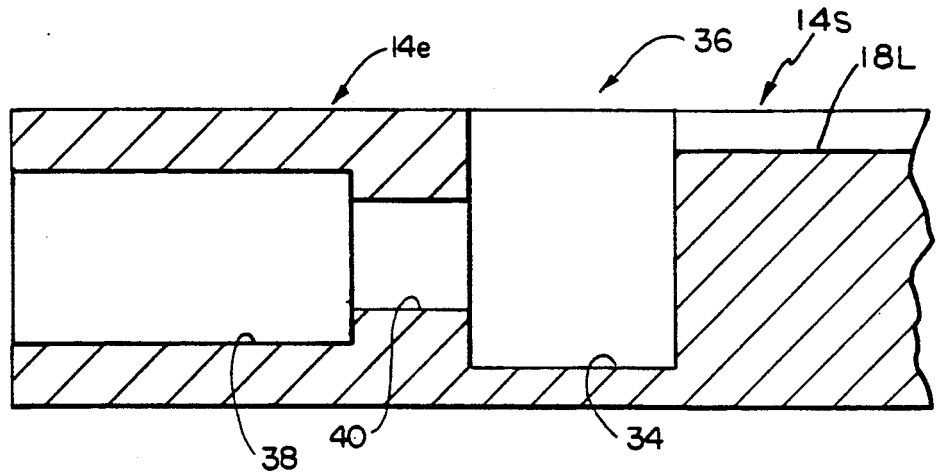
FIG. 8 is a partial cross-sectional view illustrating the integral vacuum interconnect means of the overlapped test specimen fixture taken along line 8—8 of FIG. 5.

The OTS fixture 10 also includes integral means 36 for readily interconnecting a vacuum source (not shown) to the OTS fixture 10 as illustrated in FIG. 8. The vacuum interconnect means 36 allows a vacuum line having an integral end connector (not shown), connected to the vacuum source, to be quickly and easily integrated with the OTS fixture 10. The vacuum interconnect means 36 eliminates the need to connect a vacuum source directly to the vacuum bagging material, thereby greatly improving the durability and reliability of the OTS fixture 10 over prior art systems. The vacuum interconnect means 36 of the present invention includes a connector port 38 configured to receive, in a seal-tight manner, the integral end connector attached to the vacuum line of the vacuum source. An interface channel 40 fluidically interconnects the connector port 38 to the continuous vent channel 34.

As illustrated in the embodiment of the OTS fixture 10 of FIG. 5, the vacuum interconnect means 36 is formed in one endwall 14e. This configuration is adapted to lengthwise loading of the OTS fixture 10 in an autoclave (not shown) which is the conventional industry manner for loading autoclaves. It will be appreciated, however, that the vacuum interconnect means 36 may also be formed in one of the sidewalls 14s.

To use the OTS fixture 10 of the present invention, one standardized coupon C of each pair of standardized coupons C is precisely positioned on the lower support surface 18L within the defined stalls 30 of the OTS fixture 10 as described hereinabove. The coupon securing means 32 is used to lock individual standardized coupons C, as precisely positioned, to the lower support surface 18L within the OTS fixture 10. Since the procedure for applying the adhesive system AdS to be tested and finalizing the assembly of the test specimen TS varies somewhat between paste and film adhesive systems, the different procedures for each type adhesive systems AdS will be described.

For paste adhesive systems, the paste adhesive AdS to be tested is applied to the defined overlap area OA of the standardized coupon C secured to the lower support surface 18L and to the defined overlap area OA of the standardized coupon C to be secured to the corresponding upper support surface 18U. Prior to securing the standardized coupon C to the corresponding upper support surface 18U, a scrim (not shown) may be disposed in the paste adhesive AdS applied to the defined overlap area OA of the standardized coupon C secured to the lower support surface 18L. The scrim, which is a durable, loosely woven fabric of predetermined mesh size known to those skilled in the art, is operative to retain the paste adhesive AdS within the bounds of the standardized bonding site SBS and to ensure that the paste adhesive AdS has the predetermined thickness $t_{AdS}$. The other standardized coupon C is then precisely positioned on the upper support surface 18U, as described hereinabove, to define the test specimen TS, which is then locked in place by the securing means 32.

For film adhesives AdS, the procedure is somewhat simpler. The adhesive film AdS to be tested is applied to the defined overlap area OA of the standardized coupon C secured to the lower support surface 18L. Film adhesives AdS usually have an integral scrim incorporated therein, and therefore, the film adhesive AdS is simply layed up within the bounds of the defined overlap area OA to the predetermined thickness $t_{AdS}$. The other standardized coupon C is then precisely positioned on the upper support surface 18U, as described hereinabove, to define the test specimen TS, which is locked in place by the securing means 32.

The OTS fixture 10 is then utilized to cure test specimens TS disposed therein. The procedure for accomplishing room temperature or oven curing is well known to those skilled in the art, and need not be described further herein. To utilize the OTS fixture 10 in an autoclave environment, the OTS fixture 10 is further prepared and processed as described in the following paragraphs.

Vacuum bagging material is sealed to the upper edges 14ue of the peripheral shoulder 14 for example, see FIGS. 5, 6A, 6B, of an OTS fixture 10 containing one or more test specimens TS. The types of vacuum bagging material having utility in an autoclave environment, the types of sealants, and the method of sealing are well known to those skilled in the art, and therefore, need not be described in further detail. A vacuum source is interconnected to the OTS fixture 10 via the vacuum interconnect means 36, see FIGS. 5, 8 and a vacuum drawn within the enveloped OTS fixture 10. The vacuum drawn within the enveloped OTS fixture 10, due to the configuration of the continuous vent channel 34, causes the vacuum bagging material to conformably contact test specimens TS secured within the OTS fixture 10.

The vacuumized, enveloped OTS fixture 10 is loaded into an autoclave and subjected to an autoclave-type curing cycle, e.g., variable pressures in the range of about 20 to about 60 psi and variable temperatures in the range of about 250° to about 350° F., to cure the adhesive system AdS. Variable pressures generated within the autoclave are transmitted to the exposed surfaces of the test specimens TS via the vacuum bagging material After completion of the cure cycle, the OTS fixture 10 is unloaded from the autoclave, the vacuum bagging material removed, and the cured test specimens TS released from the support surface 18, by disengaging the coupon securing means 32, and removed from the OTS fixture 10. The cured test specimens TS may be subsequently cleaved to produce overlap bonded test strips Test that may be used for characterization testing to define the properties of the adhesive bond.

The OTS fixture 10 according to the present invention consistently produces processed test specimens TS having standardized bonding sites SBS of constant overlap area OA. The utilization of the OTS fixture 10 of the present invention has reduced the number of test specimen rejects by about 50 to about 300 percent.

While the OTS fixture 10 according to the present invention has been described in terms of preparing test specimens TS in an autoclave-type curing environment, it will be appreciated that the OTS fixture 10 may also be used for room temperature and oven temperature curing of test specimens TS at constant pressure. Moreover, the OTS fixture 10 may be used with conventional bagging techniques rather than utilizing vacuum bagging material sealed to the upper edges 14ue of the fixture 10. That is, the OTS fixture 10 may be inserted into and sealed in a vacuum bag, with the vacuum line running into the vacuum bag through the sealed neck thereof.

Furthermore, although the OTS fixture 10 was described hereinabove as having utility for use with single overlapped test specimens TS, the OTS fixture 10 of the present invention may also be utilized to form double overlap test specimens TS.

The foregoing disclosure described the use of aluminum alloy standardized coupons C with the OTS fixture 10 of the present invention. It will be appreciated, however, that the OTS fixture 10 of the present invention may also be utilized with coupons that have dimensions other than those disclosed for the standardized coupon C described hereinabove. Moreover, the OTS fixture may be utilized with coupons formed from the actual structural materials of the elements to be bonded in combination. This would allow a preliminary characterization of a particular adhesive system for a specific application. Therefore, it is to be understood that the OTS fixture of the present invention is not intended to be limited to the use of aluminum alloy coupons as explicitly described hereinabove.

Although the present invention has been shown and described with respect to detailed embodiments thereof, it will be understood by those skilled in the art that various changes in form and detail of the described subject matter may be made without departing from the spirit and scope of the claimed invention.

What is claimed is:

1. An overlapped test specimen fixture for preparing at least one pair of standardized coupons as a test specimen having at least one standardized bonding site of constant bonding area with an adhesive system to be tested applied thereto, the prepared test specimen having utility for characterization testing of the adhesive system applied to the at least one standardized bonding site, each of the standardized coupons of the at least one pair having a predetermined length, a predetermined width, and a predetermined thickness, comprising:

means for supporting the standardized coupons of the at least one pair in overlapping relation with respect to one another;

means for precisely positioning the standardized coupons of the at least one pair in lengthwise relation with respect to one another wherein overlapped, precisely lengthwise positioned standardized coupons of the at least one pair demarcate a predetermined overlap length;

means for precisely positioning the standardized coupons of the at least one pair in transverse relation with respect to one another wherein overlapped, precisely transversely positioned standardized coupons of the at least one pair demarcate a predetermined overlap width;

said supporting means, said lengthwise positioning means, and said transverse positioning means being operative in combination to precisely position the standardized coupons of the at least one pair in a predetermined overlapping relation to demarcate the test specimen having the at least one standardized bonding site of constant bonding area for application of the adhesive system to be tested, the constant bonding area being defined by the predetermined overlap length and width demarcated by the standardized coupons of the at least one pair precisely positioned in the predetermined overlapping relation; and means for temporarily securing the precisely positioned, overlapped test specimen in immobile combination with said supporting means.

2. The overlapped test specimen fixture of claim 1 further comprising vent channel means formed in said supporting means for providing a continuous pathway for fluid flow from said overlapped test specimen fixture, said vent channel means underlying the precisely positioned test specimen temporarily secured in said overlapped test, specimen fixture.

3. The overlapped test specimen fixture of claim 2 further comprising means for fluidically interconnecting a vacuum source in combination with said overlapped test specimen fixture, said vacuum source interconnecting means being fluidically interconnected to said vent channel means.

4. The overlapped test specimen fixture of claim 3 further comprising means for sealing vacuum bagging material in combination with said overlapped test specimen fixture to envelop the test specimen temporarily secured to said supporting means wherein the vacuum source may be operated to draw a vacuum about the enveloped test specimen utilizing said integral interconnect means and said vent channel means so that said overlapped test specimen fixture may be cured in an autoclave environment.

5. The overlapped test specimen fixture of claim 1 further comprising means for fluidically interconnecting a vacuum source in combination with said overlapped test specimen fixture.

6. The overlapped test specimen fixture of claim 1 further comprising means for sealing vacuum bagging material in combination with said overlapped test specimen fixture to envelop the test specimen temporarily secured to said supporting means.

7. The overlapped test specimen fixture of claim 1 wherein said supporting means comprises:
 a caul plate; and
 an integral, elevated shoulder surrounding the periphery of said caul plate, said integral, elevated shoulder including opposed sidewalls and opposed endwalls;

said caul plate having an exposed surface bounded by internal faces of said opposed sidewalls and said opposed endwalls configured as a bi-level, flat support surface for supporting the standardized coupons of the at least one pair in overlapping relation, said exposed surface including a lower flat support surface for supporting one of the standardized coupons of the at least one pair and an upper flat support surface for supporting the other of the standardized coupons of the at least one pair, said upper and lower flat support surfaces being vertically spaced apart by a spacing shoulder having a predetermined height.

8. The overlapped test specimen fixture of claim 7 wherein said lengthwise precise positioning means comprises said opposed internal faces of said sidewalls.

9. The overlapped test specimen fixture of claim 7 wherein said transverse precise positioning means comprises a plurality of integrally formed locator rails extending upwardly from said upper and lower flat support surfaces.

10. The overlapped test specimen fixture of claim 9 further comprising an integral, continuous vent channel formed in said bi-level, flat support surface for providing a continuous pathway for fluid evacuation of said overlapped test specimen fixture, said continuous vent channel including segments disposed adjacent said opposed endwalls, segments disposed adjacent said plurality of integrally formed locator rails, segments disposed adjacent portions of said opposed sidewalls, and segments disposed transversely between adjacent ones of said plurality of locator rails and said opposed endwalls.

11. The overlapped test specimen fixture of claim 7 further comprising means integrally formed in one of said opposed endwalls for interconnecting a vacuum source having a connector to said overlapped test specimen fixture, said vacuum source interconnecting means including said one of said opposed endwalls having a connector port formed therein configured to sealing receive the connector of the vacuum source and having an interface channel fluidically interconnecting said connector port to said exposed surface of said caul plate.

12. The overlapped test specimen fixture of claim 11 further comprising an integral, continuous vent channel formed in said bi-level, flat support surface for providing a continuous pathway for fluid flow for said overlapped test specimen fixture, said continuous vent channel including segments disposed adjacent said opposed endwalls, segments disposed adjacent s id plurality of integrally formed locator rails, segments disposed adjacent portions of said opposed sidewalls, and segments disposed transversely between adjacent ones of said plurality of locator rails and said opposed endwalls, and wherein said interface channel of said vacuum source interconnecting means fluidically interconnects to one of said segments of said continuous vent channel disposed adjacent said endwalls 13. The overlapped test specimen fixture of claim 7 wherein said opposed sidewalls and said opposed endwalls have flat upper edges for sealing a vacuum bagging material thereto wherein said upper and lower support surfaces of said caul plate are enveloped by the vacuum bagging material.

14. A method of preparing at least one pair of standardized coupons as a test specimen having at least one standardized bonding site of constant bonding area for application of an adhesive system to be tested utilizing an overlapped test specimen fixture, comprising the steps of:

supporting the standardized coupons of the at least one pair in overlapping relation with respect to one another in said overlapped test specimen fixture;

precisely positioning the overlapped standardized coupons in lengthwise relation with respect to one another in said overlapped test specimen fixture wherein the overlapped precisely lengthwise positioned standardized coupons of the at least one pair demarcate a predetermined overlap length;

precisely positioning the overlapped standardized coupons in transverse relation with respect to one another in said overlapped test specimen fixture wherein the overlapped precisely transversely positioned standardized coupons of the at least one pair demarcate a predetermined overlap width;

temporarily securing one of the overlapped, precisely positioned standardized coupons to said overlapped test specimen fixture;

applying an adhesive system to be tested to at least one face of a standardized bonding site demarcated by the precisely positioned, overlapped standardized coupons;

temporarily securing the other of the precisely positioned, overlapped standardized coupons to said overlapped test specimen fixture, said temporarily secured, precisely positioned, overlapped standardized coupons having the adhesive system applied to the standardized bonding site defining the test specimen; and curing the test specimen to provide a cured test specimen having utility for characterization testing of the adhesive system.

* * * * *

UNITED STATES PATENT AND TRADEMARK OFFICE
CERTIFICATE OF CORRECTION

PATENT NO. : 5,142,905
DATED : Sep. 1, 1992
INVENTOR(S) : Ezzo et al.

It is certified that error appears in the above-identified patent and that said Letters Patent is hereby corrected as shown below:

Claim 10, column 14, line 27, Delete "fluid".

Claim 12, column 14, line 49, Delete "fluid flow for" and insert -- evacuation of --.

Claim 12, column 14, line 52, "s id" should read -- said --.

Signed and Sealed this

Sixth Day of September, 1994

Attest:

BRUCE LEHMAN

Attesting Officer  Commissioner of Patents and Trademarks